US009427201B2

(12) United States Patent
West et al.

(10) Patent No.: US 9,427,201 B2
(45) Date of Patent: Aug. 30, 2016

(54) NON-INVASIVE METHOD FOR USING 2D ANGIOGRAPHIC IMAGES FOR RADIOSURGICAL TARGET DEFINITION

(75) Inventors: Jay B. West, Mountain View, CA (US); Calvin R. Maurer, Jr., Mountain View, CA (US); Dongshan Fu, Santa Clara, CA (US); John R. Dooley, Castro Valley, CA (US)

(73) Assignee: Accuray Incorporated, Sunnyvale, CA (US)

( * ) Notice: Subject to any disclaimer, the term of this patent is extended or adjusted under 35 U.S.C. 154(b) by 2800 days.

(21) Appl. No.: 11/823,932

(22) Filed: Jun. 30, 2007

(65) Prior Publication Data

US 2009/0005668 A1 Jan. 1, 2009

(51) Int. Cl.
*A61B 6/00* (2006.01)
*G06T 7/00* (2006.01)
*A61B 6/02* (2006.01)

(52) U.S. Cl.
CPC ............... *A61B 6/504* (2013.01); *A61B 6/466* (2013.01); *A61B 6/481* (2013.01); *A61B 6/547* (2013.01); *A61B 6/587* (2013.01); *G06T 7/0028* (2013.01); *G06T 7/0038* (2013.01); *A61B 6/022* (2013.01)

(58) Field of Classification Search
CPC ...... A61B 6/466; A61B 6/481; A61B 6/547; A61B 6/587; A61B 6/504; A61B 6/022; G06T 7/0038; G06T 7/0028
USPC ....... 600/407, 429, 414, 424, 437, 410, 411, 600/417, 416, 521; 382/154, 128, 103; 606/130
See application file for complete search history.

(56) References Cited

U.S. PATENT DOCUMENTS

| | | | | |
|---|---|---|---|---|
| 4,617,925 A * | 10/1986 | Laitinen | ............... | A61B 19/203 606/130 |
| 5,389,101 A * | 2/1995 | Heilbrun | ............... | A61B 5/06 348/E13.014 |
| 5,588,033 A * | 12/1996 | Yeung | ............... | 378/4 |
| 6,307,914 B1 | 10/2001 | Kunieda et al. | | |
| 6,317,621 B1 * | 11/2001 | Graumann | ............... | A61B 6/12 378/62 |
| 7,474,913 B2 * | 1/2009 | Durlak | ............... | 600/428 |
| 7,684,647 B2 * | 3/2010 | Fu et al. | ............... | 382/294 |
| 7,739,090 B2 * | 6/2010 | Charbel et al. | ............... | 703/11 |
| 7,894,647 B2 * | 2/2011 | Zhou et al. | ............... | 382/128 |
| 7,903,856 B2 * | 3/2011 | Pfister et al. | ............... | 382/128 |
| 8,055,044 B2 * | 11/2011 | Mielekamp | ............... | 382/130 |
| 2002/0045817 A1 * | 4/2002 | Ichihashi | ............... | 600/425 |
| 2002/0136356 A1 * | 9/2002 | Vallin et al. | ............... | 378/205 |
| 2005/0013681 A1 * | 1/2005 | Carvalho | ............... | F16B 39/34 411/438 |

(Continued)

OTHER PUBLICATIONS

M. Vermandel et al., "A 2D/3D Matching Based on a Hybrid Approach: Improvement to the Imaging flow for AVM Radiosurgery", Proceedings of the 2005 IEEE, Engineering in Medicine and Biology 27th Annual Conference, Shanghai, China, Sep. 1-4, 2005, pp. 3071-3073.

(Continued)

*Primary Examiner* — Long V Le
*Assistant Examiner* — Colin T Sakamoto
(74) *Attorney, Agent, or Firm* — Lowenstein Sandler LLP

(57) ABSTRACT

A non-invasive method and system for using 2D angiographic images for radiosurgical target definition uses non-invasive calibration devices and methods to calibrate an angiographic imaging system and a six-parameter registration algorithm to register angiographic images with 3D scan data for radiation treatment planning.

24 Claims, 10 Drawing Sheets

(56) References Cited

U.S. PATENT DOCUMENTS

| | | | |
|---|---|---|---|
| 2005/0049486 A1* | 3/2005 | Urquhart et al. | 600/429 |
| 2006/0257006 A1* | 11/2006 | Bredno et al. | 382/128 |
| 2007/0009080 A1* | 1/2007 | Mistretta | 378/4 |
| 2007/0110289 A1* | 5/2007 | Fu et al. | 382/128 |
| 2007/0127845 A1* | 6/2007 | Fu et al. | 382/294 |

OTHER PUBLICATIONS

Maximilien Vermandel et al, "Registration, Matching, and Data Fusion in 2D/3D Medical Imaging: Application to DSA and MRA", Laboratoire de Biophysique—ITM, UPRES EA 1049, Pavillon Vancostenobel, University Hospital, F-59037 cedex, Lille, France, R.E. Ellis and T.M. Peters (Eds.): MICCAI 2003, LNCS 2878, pp. 778-785, 2003. Copyright Springer-Verlag Berlin Heidelberg 2003.

D. Gibon, Ph.D et al., "Stereotactic Localization in Medical Imaging: A Technical and Methodological Review", Journal of Radiosurgery, vol. 2, No. 3, 1999, Copyright 1999 Plenum Publishing Corporation, pp. 167-180.

Zhengyou Zhang, Senior Member, IEEE, "A Flexible New Technique for Camera Calibration", IEEE Transactions on Pattern Analysis and Maching Intelligence, vol. 22, No. 11, Nov. 2000, pp. 1330-1334.

Roger Y. Tsai, "A Versatile Camera Calibration Technique for High-Accuracy 3D Machine Vision Metrology Using Off-the-Shelf TV Cameras and Lenses", IEEE Journal of Robotics and Automation, vol. RA-3, No. 4, Aug. 1987, Copyright 1987 IEEE, pp. 323-344.

E Coste-Maniere et al., "Robotic Whole Body Stereotactic Radiosurgery: Clinical Advantages of the CyberKnife® Integrated System", Paper Accepted: Dec. 1, 2004, Published online: Jan. 15, 2005. Copyright 2005 Robotic Publications Ltd., Available from: www.roboticpublications.com, Int J Medical Robotics and Computer Assisted Surgery 2005; 1(2); 28-39.

\* cited by examiner

NON-INVASIVE METHOD FOR USING 2D ANGIOGRAPHIC IMAGES FOR RADIOSURGICAL TARGET DEFINITION

TECHNICAL FIELD

Embodiments of the present invention are related to the field of medical imaging and data fusion, in particular, to non-invasive methods and apparatus for combining 2D angiographic images with 3D scan data for radiosurgical target definition.

BACKGROUND

External beam radiation treatment is a non-invasive treatment method for pathological anatomies such as benign or malignant tumors, lesions and arteriovenous malformations (AVMs), which use a precisely positioned radiation beam to necrotize pathological tissue.

In one type of external beam radiation treatment, an external radiation source is mounted in a gantry that is rotated around a center of treatment (isocenter) and directs a sequence of x-ray beams at a pathological anatomy from multiple angles, with the patient positioned so the pathological anatomy is at the isocenter. As the angle of the radiation source changes, every beam passes through the pathological anatomy, but passes through a different area of healthy tissue on its way to the pathological anatomy. As a result, the cumulative radiation dose at the pathological anatomy is high and the average radiation dose to healthy tissue is low. In some systems, the radiation source includes a multi-leaf collimator (MLC) that may be used to shape the radiation beam.

In another type of external beam radiation treatment (e.g., the CYBERKNIFE® Robotic Radiosurgery System manufactured by Accuray Incorporated of Sunnyvale, Calif.), the radiation source is mounted on a robotic control arm with multiple degrees of freedom, allowing the treatment to be non-isocentric to achieve better dose conformality and homogeneity relative to isocentric systems.

The application of either type of treatment (i.e., isocentric or non-isocentric) is preceded by a diagnostic and treatment planning phase where a medical physicist determines the appropriate radiation dose for the pathological anatomy and plans the sequence of radiation treatment beams (e.g., position, location, angle, duration and shape) to achieve the prescribed dose.

In forward treatment planning, the medical physicist determines parameters such as the trajectory and duration of the radiation beams to be applied to a pathological anatomy and then calculates how much radiation will be absorbed by pathological tissue, critical structures (i.e., vital organs) and other healthy tissue. The parameters describing the beams may then be successively updated by the physicist until the radiation dose distribution is deemed acceptable.

In inverse planning, in contrast to forward planning, the medical physicist specifies the minimum dose to the tumor and the maximum dose to other healthy tissues independently, and the treatment planning software then selects the direction, distance, and total number and energy of the beams in order to achieve the specified dose conditions.

Conventional treatment planning systems are designed to import three-dimensional (3D) images from a diagnostic imaging source such as computerized x-ray tomography (CT) scans. CT is able to provide an accurate three-dimensional model of a volume of interest (e.g., skull or other region of interest of the body) generated from a collection of CT slices and, thereby, the volume requiring treatment can be visualized in three dimensions.

For most applications in radiosurgical treatment planning, it is sufficient to delineate anatomical structures on planar two-dimensional (2D) slices of 3D CT image volumes, with the possible additional steps of viewing renderings of the structures in the space of the 3D volumes during or after the delineation step. However, for some applications, such as treating cranial arteriovenous malformations (AVMs), for example, 3D CT images are not always sufficient for target delineation.

An AVM is a congenital disorder of the connections between veins and arteries in the vascular system. Normally, the arteries in the vascular system carry oxygen-rich blood at a relatively high pressure. Structurally, arteries divide and sub-divide repeatedly, eventually forming a sponge-like capillary bed. Blood moves through the capillaries, giving up oxygen and taking up waste products from the surrounding cells. Capillaries successively join together, one upon the other, to form the veins that carry blood away at a relatively low pressure.

In an AVM, the arteries are connected directly to the veins in a tangled interconnection and the capillary bed is missing. The tangle of blood vessels forms a relatively direct connection between high pressure arteries and low pressure veins. This collection of blood vessels, known as a nidus, can be extremely fragile and prone to bleeding. AVMs can occur in various parts of the body including the brain, where bleeding can cause severe and often fatal strokes. If detected before a stroke occurs, the AVM can be treated with external beam radiation. The radiation damages the walls of the veins and arteries of the nidus. In response, the walls thicken and grow in, eventually closing off the arteries feeding blood into the nidus.

With respect to AVMs, one of the goals of treatment planning is to identify the nidus of the AVM and to distinguish it from its feeding vessels. However, identifying the nidus and its feeder vessels in a CT scan is difficult because the target vasculature has very low contrast in the x-ray modality of CT scans. In order to visualize the AVM, including the nidus and the feeding vessels, the patient can be injected with an x-ray contrast agent immediately prior to CT imaging. However, because of the technical limitations on image acquisition speed of 3D CT images, the 3D images generally show the AVM after the contrast agent has suffused the nidus. While it is sometimes possible to delineate the nidus from the 3D images, it may often be difficult to distinguish the feeding vessels from the nidus and to identify the boundary between the nidus and the feeding vessels.

As an alternative, the patient may be imaged in a separate 2D angiographic imaging system, which may include a fixed x-ray source and detector or, alternatively, a source and detector that are movable around the patient to capture different views. Images can be acquired both before and after the injection of the contrast agent. The 'before' image can be subtracted from the 'after' image to produce a difference image known as a digital subtraction angiography (DSA) image.

In order to distinguish the feeding vessels from the nidus, a rapid series of fixed, 2D x-ray projection images can be taken from the time the contrast agent is injected until it enters the nidus. The 2D images can then be examined after the fact to show the contrast agent advancing through the feeding vessels and entering the nidus. The image that best distinguishes the feeding vessels from the nidus can then be selected from the sequence.

In order for the 2D angiograms to be useful for radiosurgical treatment planning, they need to be integrated with the 3D CT scan data. However, the imaging geometry of the angiographic imaging system (e.g., imaging angles and source and detector separations) may be unknown with respect to the imaging geometry of the CT imaging system, so that the two sets of images cannot be directly integrated. Conventionally, in the case of cranial AVMs, the patient is fitted with an invasive frame that holds a configuration of fiducial markers. The attachment points of the frame are sharply pointed screws that pierce the skin and enter the skull of the patient. The fiducial markers then appear as landmarks in the angiographic images. The frame remains attached to the patient during a subsequent CT scan so that the landmarks appear in the CT images. Different slices of the CT image can then be iteratively compared with the angiographic images to find a matching orientation. The frame may also be required for patient alignment during treatment, requiring the patient to suffer the discomfort of the invasive frame continuously through the process of diagnostic imaging, treatment planning and treatment delivery.

DESCRIPTION OF THE DRAWINGS

The present invention is illustrated by way of example, and not by way of limitation, in the figures of the accompanying drawings, in which.

DETAILED DESCRIPTION

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. As used herein, the term "image" may mean a visible image (e.g., displayed on a video screen) or a digital representation of an image (e.g., a file corresponding to the pixel output of an image detector). Unless stated otherwise as apparent from the following discussion, it will be appreciated that terms such as "generating," "registering," "determining," "aligning," "positioning," "processing," "computing," "selecting," "estimating," "comparing," "tracking" or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

Figure 1:
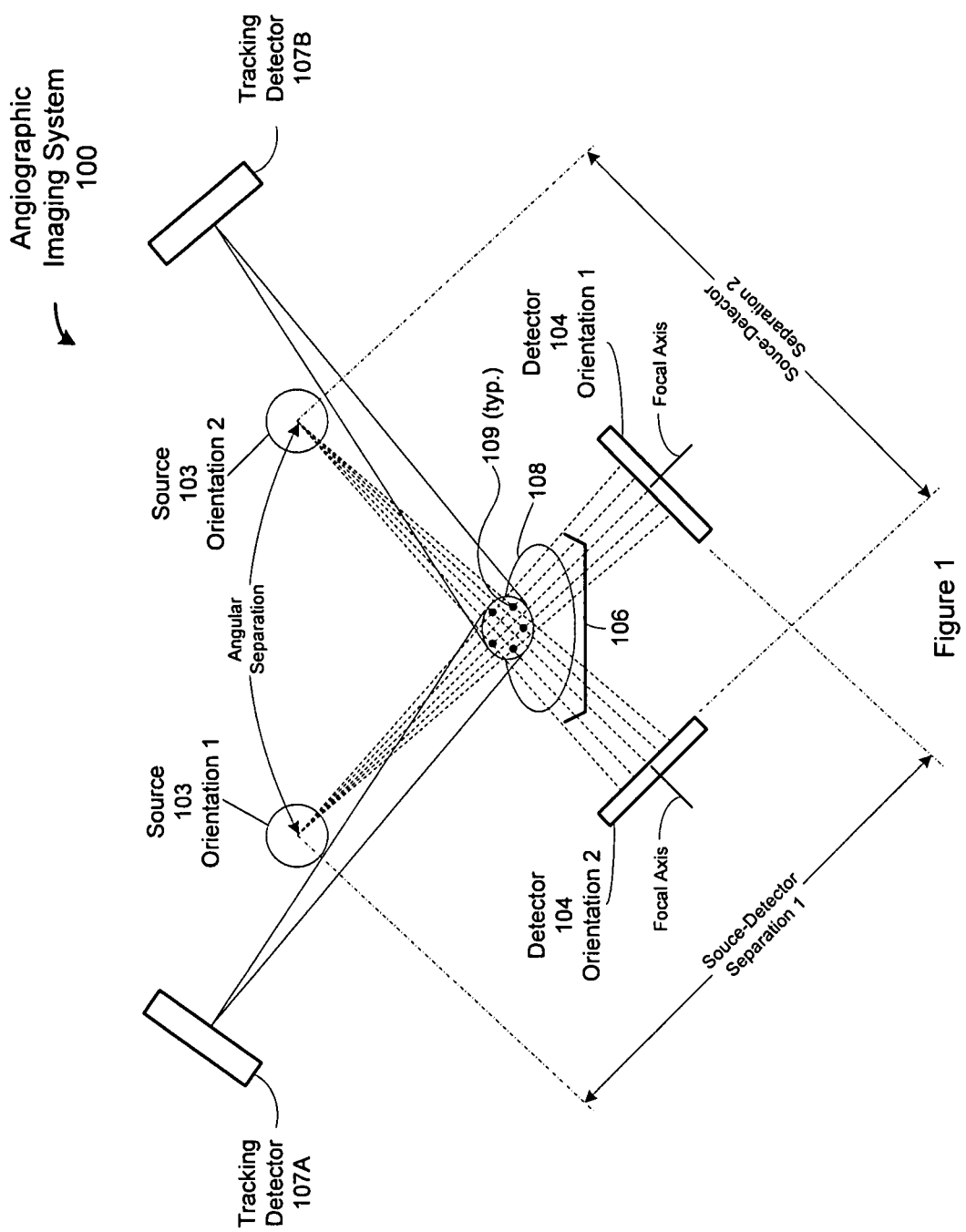
FIG. 1 illustrates an angiographic imaging system in one embodiment.

Non-invasive methods and systems for using 2D angiographic images for radiosurgical target definition are described. FIG. 1 illustrates an angiographic imaging system 100 in one embodiment. As illustrated in FIG. 1, angiographic imaging system 100 includes an x-ray source 103 and an x-ray detector 104 that can be positioned in two (or more) different orientations, characterized by an angular separation, source to detector separation, intersection of the focal axis with the detector and detector pixel size, some or all of which may not be known a priori. A patient 108 is positioned on a patient couch 106, with a fitted headrest (not shown) designed to keep the patient's head immobile. An array of non-invasive fiducial markers (109) is placed on the patient's head. The fiducial markers may be attached, for example, with adhesives.

In one embodiment, a plurality of 2D angiograms is acquired in two or more orientations of the angiographic imaging system, such that each of the plurality of 2D angiographic images includes a projection of the array of non-invasive fiducial markers. After the 2D angiographic images are acquired, the patient may be transferred to a calibrated 3D imaging system (such as a CT system, for example), where a calibrated image of the patient, including the array of fiducial markers, can be acquired. The calibrated image may then be used to measure the 3D configuration of the array of fiducial markers.

Given the measured 3D configuration of the array of fiducial markers, and the positions of the non-invasive fiducial markers in the plurality of 2D angiographic images, the imaging geometry of each of the orientations of the angiographic imaging system may be determined (i.e., the system may be calibrated) using algorithms that are known in the art (see, e.g., Roger E. Tsai, "A Versatile Camera Calibration Technique for High-Accuracy 3D Machine Vision Metrology Using Off-the-Shelf TV Cameras and Lenses," IEEE Journal of Robotics and Automation, August 1987).

Figure 2:
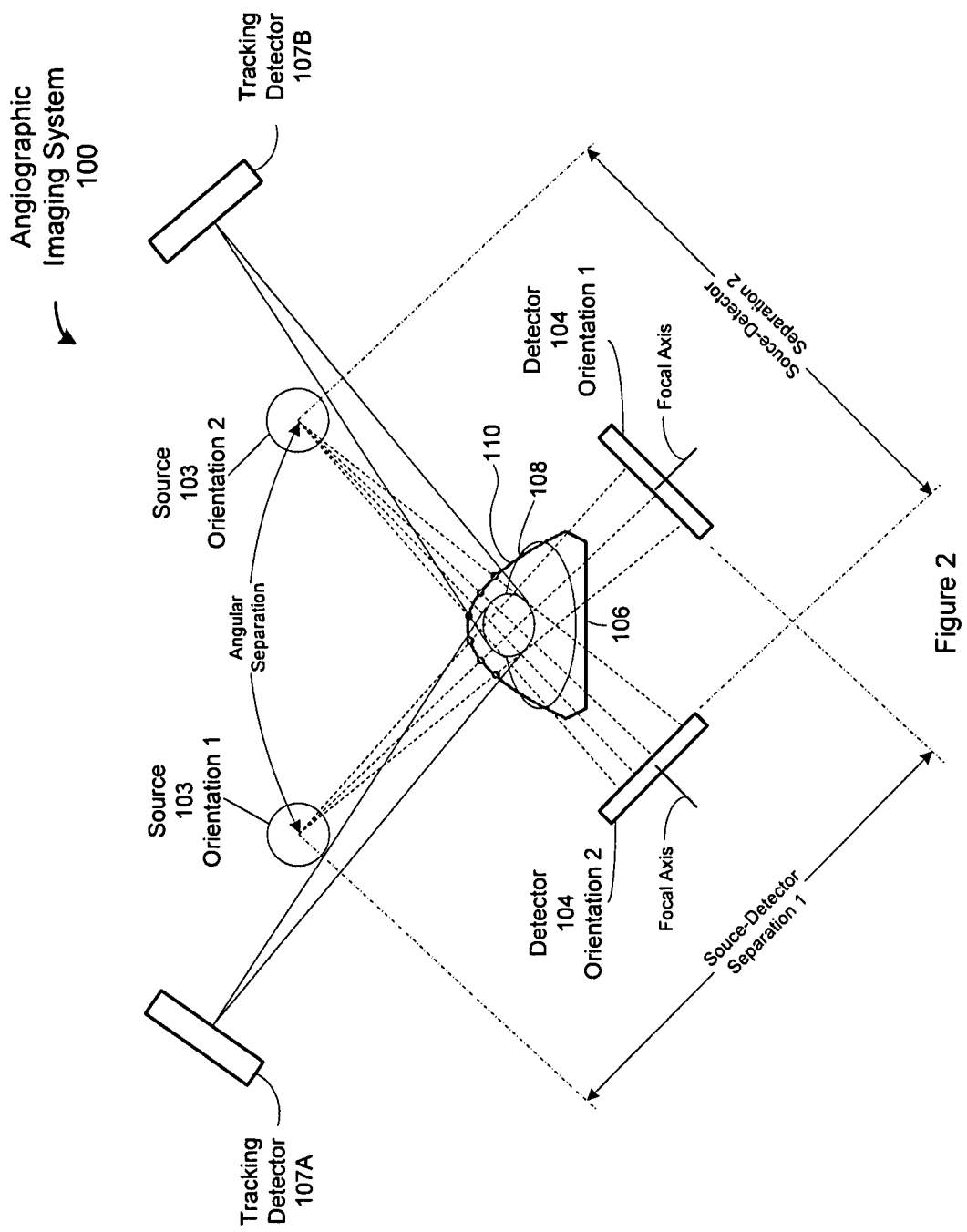
FIG. 2 illustrates an angiographic imaging system in another embodiment.

In another embodiment, as illustrated in FIG. 2, the attached array of fiducial markers 109 may be replaced with a non-invasive calibration device 110 having an array of non-invasive fiducial markers in a known 3D configuration.

In this embodiment, the imaging geometry of the angiographic imaging system may be determined directly from the known 3D configuration of the fiducial markers and the positions of the fiducial markers in the plurality of 2D angiographic images using the calibration algorithm.

In yet another embodiment, as illustrated in FIGS. 1 and 2, angiographic imaging system 100 may also include tracking detectors 107A and 107B. Tracking detectors 107A and 107B may be, for example, optical or magnetic tracking detectors as are known in the art. In this embodiment, the non-invasive fiducial markers 109 and/or the non-invasive fiducial markers on the calibration device 110 may be optical or magnetic devices that may be tracked by tracking detectors 107A and 107B to determine the 3D configuration of the fiducial markers. In this embodiment, the imaging geometry of the angiographic imaging system may be determined directly from the known (i.e. tracked) 3D configuration of the fiducial markers and the positions of the fiducial markers in the plurality of 2D angiographic images using the calibration algorithm.

Figure 3:
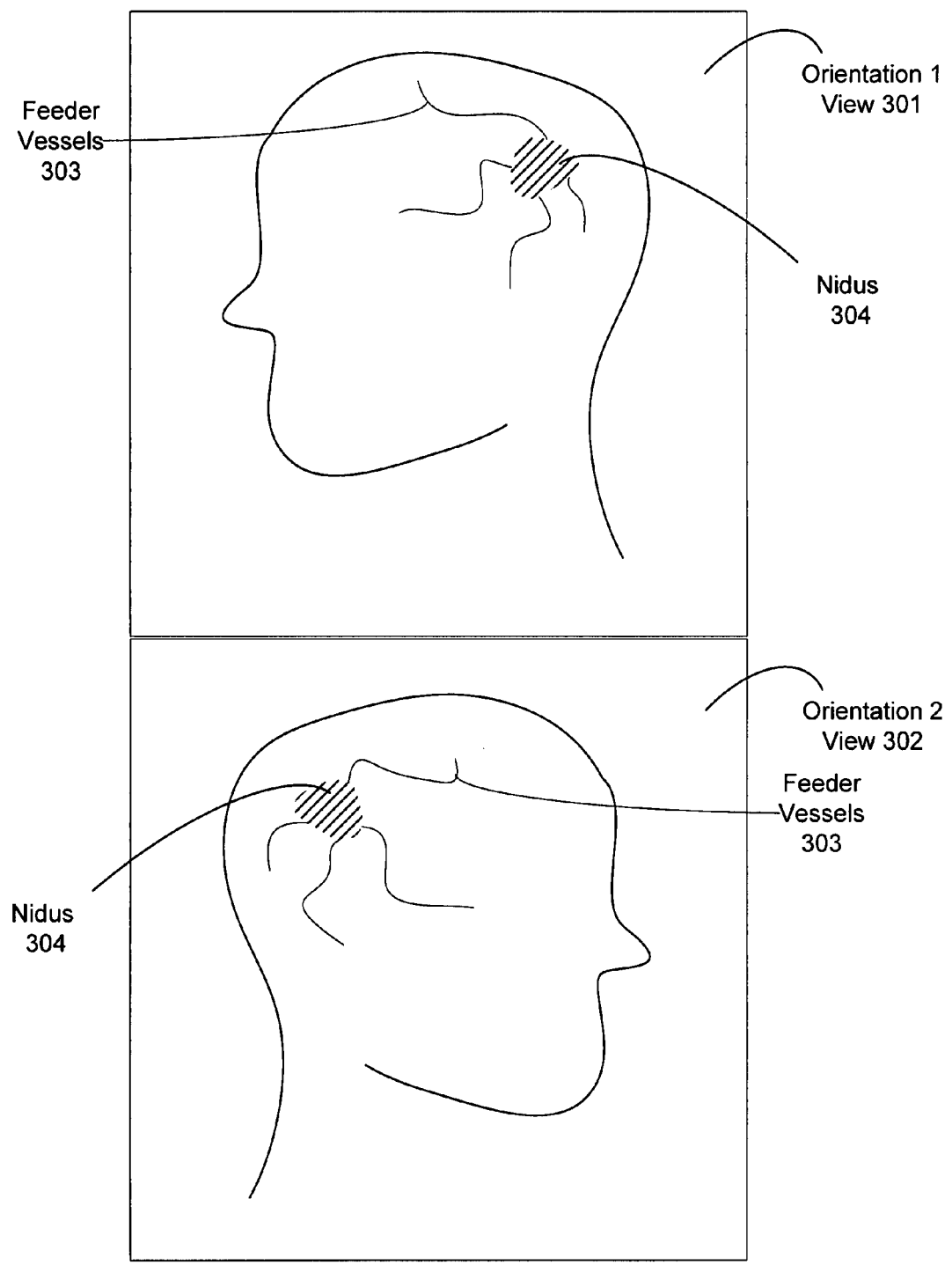
FIG. 3 illustrates a cranial arteriovenous malformation.

Once the imaging geometry of each of the orientations of the 2D angiographic imaging system are determined, the plurality of 2D angiographic images can be used to delineate the nidus of an AVM in a calibrated 3D object space. FIG. 3 is a schematic representation of an exemplary 2D angiogram in each of two orientations (views 301 and 302, respectively) of angiographic imaging system 100, illustrating a nidus 304 and feeder vessels 303. The exemplary angiograms may be selected, for example, from one or more time-series of angiograms recording the progress of a contrast agent from its injection into the patient through its infusion of the nidus. In one embodiment, the selected angiograms may be selected at a point in time where the contrast agent has just reached the nidus and defines the boundary points of the nidus in each of the 2D projections of the angiographic images. The boundary points can be connected to define a boundary contour in each projection. Given the known imaging geometry of the angiographic imaging system 100 (based on the calibration methods described above), the contours of the nidus can be back-projected through the imaging geometry of each of the two (or more) orientations of the angiographic imaging system to render a bounding volume of the nidus in the 3D object space of the angiographic imaging system.

In one embodiment, the plurality of 2D angiographic images may be imported into a treatment planning system, registered with 3D scan data of the patient as described below and combined (fused) with the 3D scan data. Registration is the determination of a one-to-one mapping or transformation between the coordinates in one space and those in another space, such that points in the two spaces that correspond to the same anatomical point are mapped to each other. To make the registration beneficial in terms of medical diagnosis or treatment planning, the transformation or mapping that the registration produces must be applied in a clinically meaningful way. For example, fusion of one image with another image to which it has been registered and reformatted may be accomplished, for example, by simply summing intensity values in the two images voxel by voxel (a "voxel," as known in the art, is a 3D volume element), by superimposing outlines (e.g., contours) from one image on the other image, by encoding one image in hue and the other in brightness in a color image, or by providing a pair of movable cursors on two views linked via the registering transformation so that the cursors are displayed at corresponding points. Other fusion methods as are known in the art are contemplated embodiments of the inventions. In the embodiment described herein, the registration is the mapping that aligns the 3D coordinate system of the CT scan volume) with the 3D object space of the angiographic imaging system in which the 2D images were produced. The registration may be accomplished by comparing the 2D projection images from the angiographic imaging system with virtual 2D images synthesized from the 3D scan data, known as digitally reconstructed radiographs (DRRs).

A DRR is a synthetic x-ray image generated by casting (mathematically projecting) rays through the 3D scan data, simulating the geometry of the angiographic imaging system. The resulting DRR then has the same scale and point of view as the angiographic imaging system, and can be compared with the 2D angiographic images to determine the position and orientation of the patient within the angiographic imaging system. Different patient poses in the angiographic imaging system are simulated by performing 3D transformations (rotations and translations) on the 3D imaging data before each DRR is generated.

Each comparison of a 2D angiographic image with a DRR produces a similarity measure or equivalently, a difference measure, which can be used to search for a 3D transformation that produces a DRR with a higher similarity measure to the angiographic image. When the similarity measure is sufficiently maximized (or equivalently, a difference measure is minimized), the corresponding 3D transformation can be used to align the 3D object space of the angiographic imaging system with the 3D scan volume. The two data sets can then be fused to define the target anatomy (e.g., the nidus) for treatment planning.

Figure 4:
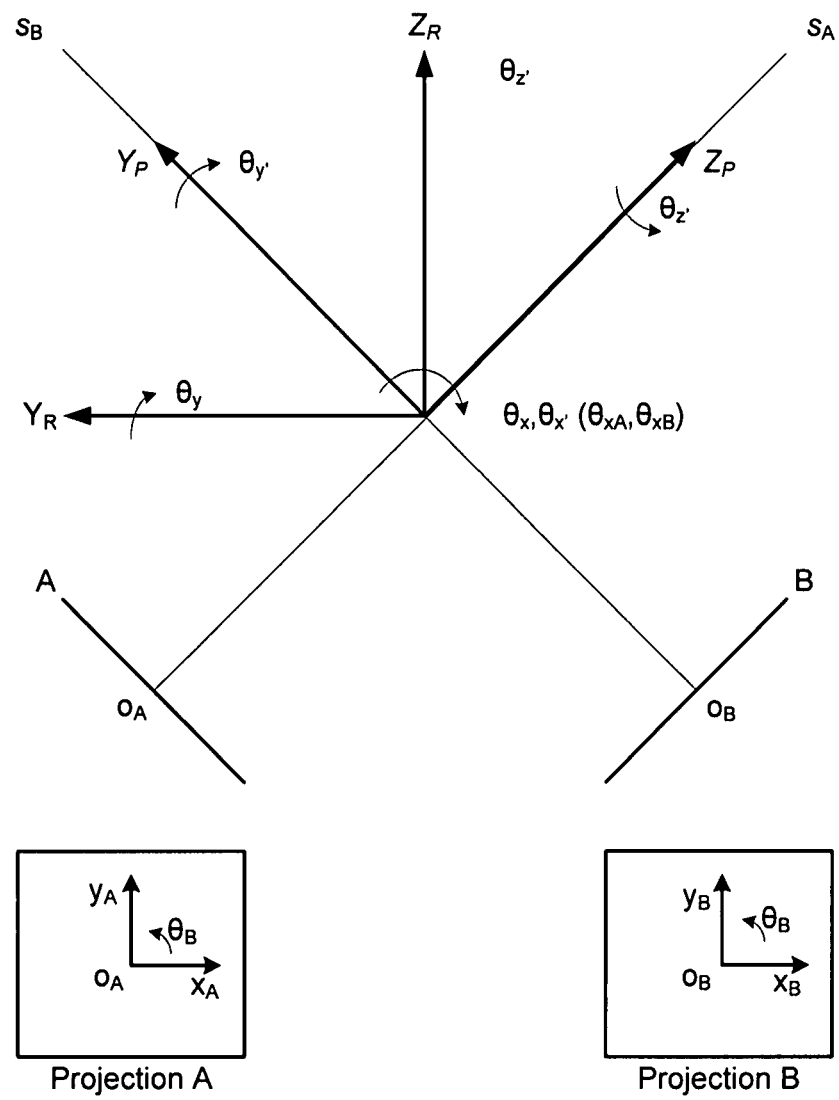
FIG. 4 illustrates the transformation parameters between an angiographic imaging system and a 3D imaging system in one embodiment.
Figure 5A:
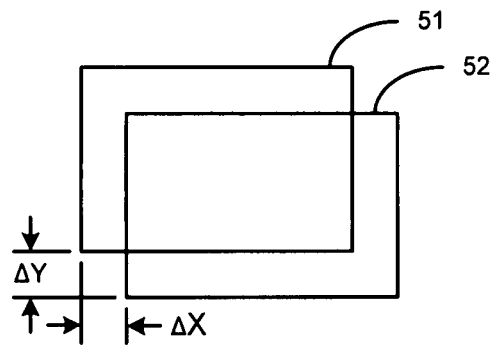
FIG. 5A illustrates in-plane translation in 2D-2D registration in one embodiment.
Figure 5B:
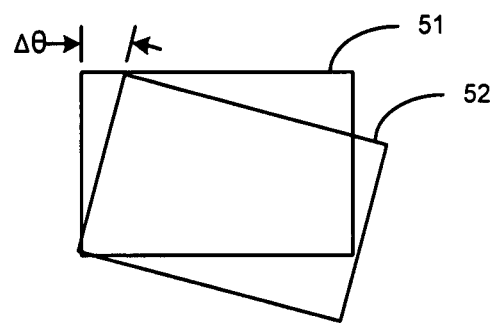
FIG. 5B illustrates in-plane rotation in 2D-2D registration in one embodiment.
Figure 5C:
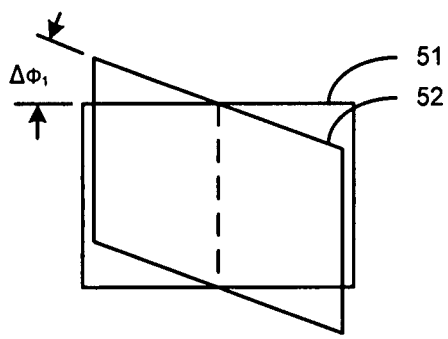
FIG. 5C illustrates a first out-of-plane rotation in 2D-2D registration in one embodiment.
Figure 5D:
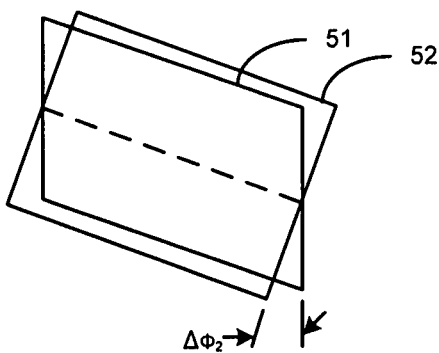
FIG. 5D illustrates a second out-of-plane rotation in 2D-2D registration in one embodiment.

FIG. 4 illustrates 3D transformation parameters between the 3D object space $[X_P,Y_P,Z_P]$ of angiographic imaging system 100 having two 2D projections and a 3D coordinate system $[X_R,Y_R,Z_R]$ associated with 3D scan data (in FIG. 4, the x-coordinates of both coordinate systems are normal to, and pointing into the plane of FIG. 4). Projections A and B in FIG. 4 are associated with the two positions of detector 104 in imaging system 100 where $S_A$ and $S_B$ represent the two positions of x-ray source 103. $O_A$ and $O_B$ are the centers of the imaging planes of the x-ray detector in the two positions. In FIG. 4, the projections A and B are viewed from the directions $O_A S_A$ and $O_B S_B$, respectively. In the example of FIG. 4, the angular separation of the two source-detector positions is shown as 90 degrees for ease of illustration, and the following equations are derived for this configuration. Other imaging geometries are possible and the corresponding equations may be derived in a straightforward manner by one having ordinary skill in the art.

A 3D transformation may be defined from coordinate system $[X_P,Y_P,Z_P]$ (having coordinates x',y',z') to coordinate system $[X_R,Y_R,Z_R]$ (having coordinates x,y,z) in FIG. 4 in terms of six parameters: three translations $(\Delta x, \Delta y, \Delta z)$ and three rotations $(\Delta\theta_x, \Delta\theta_y, \Delta\theta_z)$. A 3D rigid transformation between the two 3D coordinate systems can be derived from basic trigonometry as:

$$x = x', y = (y' - z')/\sqrt{2}, z = (y' + z')/\sqrt{2},$$

$$\theta_x = \theta_{x'}, \theta_y = (\theta_{y'} - \theta_{z'})/\sqrt{2}, \theta_z = (\theta_{y'} + \theta_{z'})/\sqrt{2}. \quad (1)$$

In the 2D coordinate system $(x_A, y_A)$ for projection A, the 3D rigid transformation may be decomposed into an in-plane transformation $(\Delta x_A, \Delta y_A, \Delta\theta_A)$ and two out-of-plane rotations $(\Delta\theta_{x_A}, \Delta\theta_{y'})$. Similarly, in the 2D coordinate system $(x_B, y_B)$ for projection B, the decomposition consists of the in-plane transformation $(\Delta x_B, \Delta y_B, \Delta\theta_B)$ and two out-of-plane rotations $(\Delta\theta_{x_B}, \Delta\theta_{z'})$. FIGS. 5A through 5D illustrate the in-plane transformations and out-of-plane rotations described herein, where a 2D x-ray image is represented by plane 51 and the 2D DRR is represented by plane 52. The 3D rigid transformation of equation (1) may be simplified by noting that the use of two projections over-constrains the solution to the six parameters of the 3D rigid transformation. The translation $x_A$ in projection A is the same parameter as $x_B$ in projection B, and the out-of-plane rotation $\theta_{x_A}$ in projection A is the same as $\theta_{x_B}$ in projection B. If $\alpha_A$ and $\alpha_B$ are geometric amplification factors (e.g., scale factors related to source-to-patient and patient-to-detector distances) for projections A and B, respectively, then the translations between the coordinate system [x'y'z'] and the 2D coordinate systems have the following relationships:

$$\Delta x' = (\alpha_B \Delta x_B - \alpha_A \Delta x_A)/2, \Delta y' = \alpha_A \Delta y_A, \Delta z' = \alpha_B \Delta y_B. \quad (2)$$

For projection A, given a set of DRR images that correspond to different combinations of the two out-of-plane rotations $(\Delta\theta_{x_A}, \Delta\theta_{y'})$, the 2D in-plane transformation $(\Delta x_A, \Delta y_A, \Delta\theta_A)$ may be estimated by a 2D to 2D image comparison, and the two out-of-plane rotations $(\Delta\theta_{x_A}, \Delta\theta_{y'})$ may be calculated by matching the angiographic image to the set of DRR images as described below, using similarity measures. Likewise, the same process may be used to solve the 2D in-plane transformation $(\Delta x_B, \Delta y_B, \Delta\theta_B)$ and the out-of-plane rotations $(\Delta\theta_{x_B}, \Delta\theta_{z'})$ for the projection B. As described below, the in-plane transformation and out-of-plane rotations may be obtained by registration between the angiographic image and a DRR, independently for both projection A and projection B. When a DRR image with a matching out-of-plane rotation is identified, the in-plane rotation and the out-of-plane rotation have the following relationships:

$$\Delta\theta_{y'} = \Delta\theta_B, \Delta\theta_{z'} = \Delta\theta_A. \quad (3)$$

If the out-of-plane rotation $\theta_{y'}$ is ignored in the set of reference DRR images for projection A, the in-plane transformation can be approximately described by $(\Delta x_A, \Delta y_A, \Delta\theta_A)$ when $\theta_{y'}$ is small (e.g., less than 5°). Once this simplifying assumption is made, and given a set of reference DRR images which correspond to various out-of-plane rotations $\Delta\theta_{x_A}$, the in-plane transformation $(\Delta x_A, \Delta y_A, \Delta\theta_A)$ and the out-of-plane rotation $\Delta\theta_{x_A}$ may be found by one or more search methods as are known in the art. These methods generally employ the calculation of a similarity measure, followed by the application of a gradient search algorithm to maximize the similarity between the in-treatment x-ray images and selected DRRs. Examples of similarity measures include (but are not limited to) normalized cross-section, entropy of the difference image, mutual information, gradient correlation, pattern intensity and gradient difference. A corresponding simplification may be made for projection B.

Given the results $(\Delta x_A, \Delta y_A, \Delta\theta_A, \Delta\theta_{x_A})$ in projection A and $(\Delta x_B, \Delta y_B, \Delta\theta_B, \Delta\theta_{x_B})$ in projection B, the approximation of the 3D rigid transformation in the 3D image coordinate system may be obtained using the following expressions:

$$\Delta x = (-\alpha_A \Delta x_A + \alpha_B \Delta x_B)/2, \Delta y = (\alpha_A \alpha y_A - \alpha_B \Delta y_B)/\sqrt{2}, \Delta z = (\alpha_A \Delta y_A + \alpha_B \Delta y_B)/\sqrt{2}, \Delta\theta_x = (\Delta\theta_{x_A} + \Delta\theta_{x_B})/2, \Delta\theta_y = (\Delta\theta_B - \Delta\theta_A)/\sqrt{2}, \Delta\theta_z = (\Delta\theta_B + \Delta\theta_A)/\sqrt{2}. \quad (4)$$

Thus, the six-parameter, 3D transformation required to align the 3D coordinate system of the angiographic imaging system with the 3D coordinate system of a 3D scan volume may be completely defined by the two sets of four parameters $(\Delta x_A, \Delta y_A, \Delta\theta_A, \Delta\theta_{x_A})$ and $(\Delta x_B, \Delta y_B, \Delta\theta_B, \Delta\theta_{x_B})$.

Figure 6:
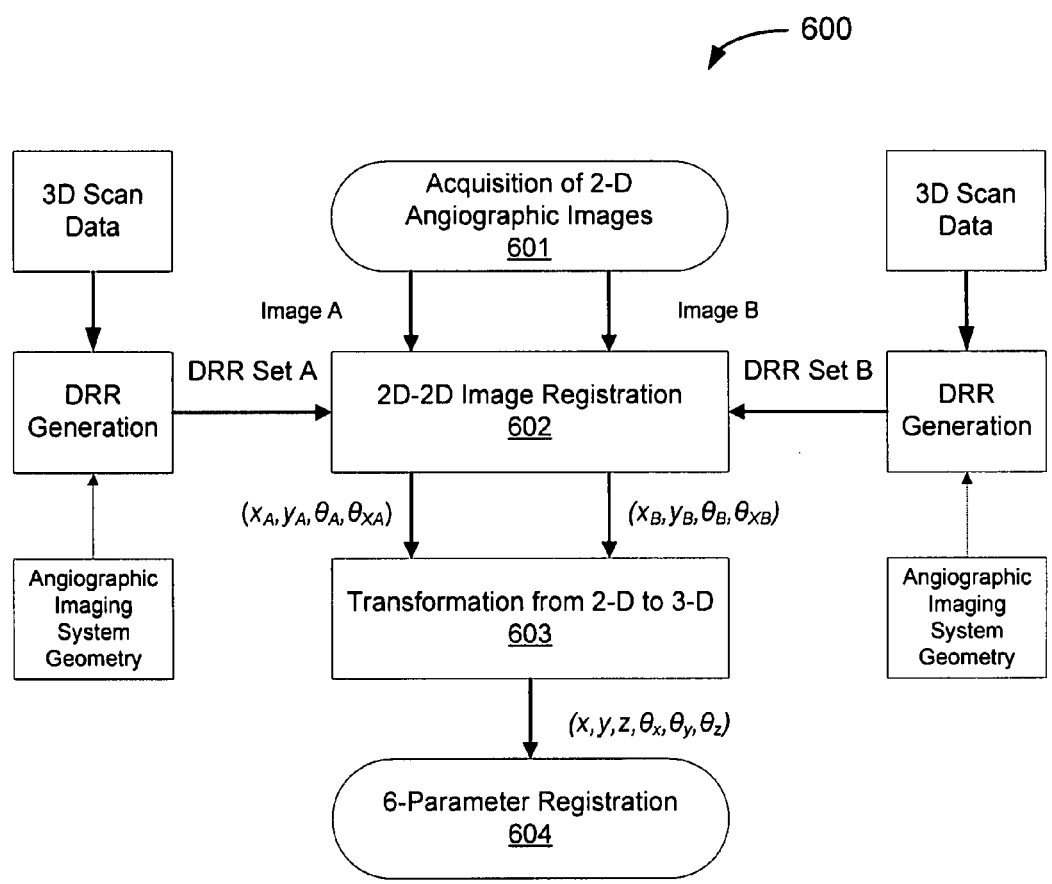
FIG. 6 is a flowchart illustrating six-parameter 2D to 3D registration in one embodiment.

The registration process described above is illustrated in the flowchart of FIG. 6. The process begins with the acquisition of the 2D angiographic projection images in two orientations (operation 601). In operation 602, 2D angiographic projection images are compared and registered, as described above, with DRR sets created from 3D scan data, based on the derived imaging geometry of the angiographic imaging system. The results of the registration are the 2 sets of 2D transformation parameters that are used in operation 603 to calculate the six parameter, 3D transformation required in operation 404 to align the 3D object space of the angiographic imaging system with the 3D coordinate system of the 3D scan volume.

Using synthetic x-rays (i.e., DRRs) to compare with the 2D angiographic images will generally result in the best (i.e., highest value) similarity measures because the angiographic images are also x-rays and will have very similar intensity patterns everywhere except where the contrast agent is present. If the field of view of the DRRs and the angiographic images are large compared with the size of the nidus and the feeder vessels, then pattern intensity matching can be performed using images where contrast agent is present. In some cases, however (e.g., when the field of view is small an/or the nidus and feeder vessels dominate image, the presence of contrast agent may interfere with registration. In these cases, the images with contrast agent may be replaced with images from the same orientation, but without the presence of contrast agent (e.g., images in a time-series taken before the injection of the contrast agent). Then, after the registration is performed as described above, the images with contrast agent may be used to define contours of the target vasculature (nidus) as described below.

Other ways of determining transformations as are known in the art are contemplated in one or more embodiments of the invention. In one embodiment, the 2D x-ray images in each projection of the x-ray imaging system may be combined for direct 2D-3D registration with the pre-operative 3D scan data as described in copending U.S. patent application Ser. No. 11/281,106.

After the transformation between the 3D object space of the angiographic imaging system and the 3D space of the CT scan volume is determined, it may be applied to the 3D object space to align the bounding volume of the nidus of the AVM with the CT scan volume. The bounding volume may be used to define contours of the targeted vasculature (nidus) in 2D slices of the 3D scan volume in, for example, axial, sagittal and coronal views. The contours may be interpolated between slices of the CT scan volume to define the target for treatment planning and treatment delivery.

Figure 7:
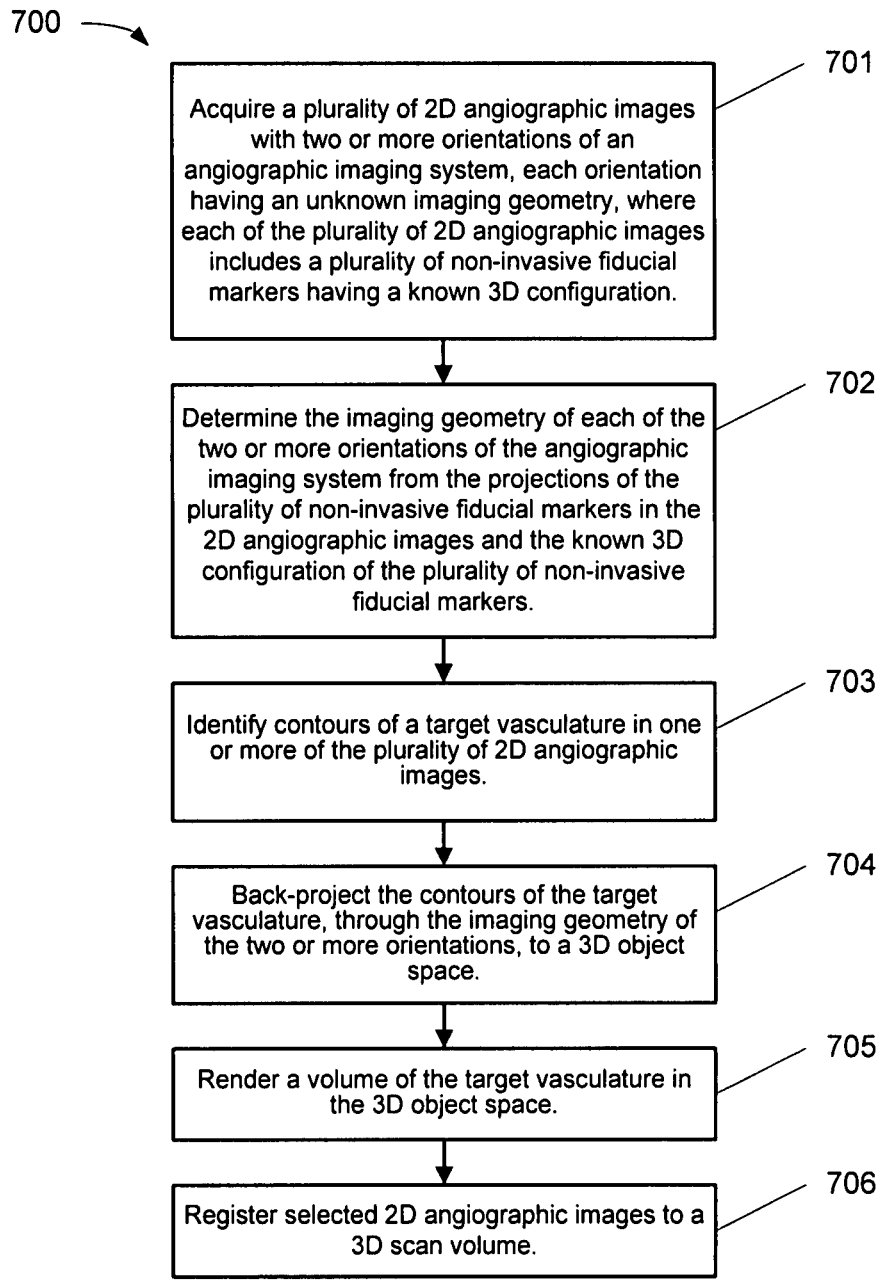
FIG. 7 is a flowchart illustrating a method in one embodiment.

FIG. 7 is a flowchart illustrating a method 700 in one embodiment of the present invention. The method begins by acquiring a plurality of two-dimensional (2D) angiographic images with two or more orientations of an angiographic imaging system, where each orientation has an unknown imaging geometry, and where each of the plurality of 2D angiographic images includes a projection of a plurality of non-invasive fiducial markers having a known three-dimensional (3D) configuration (operation 701). The method continues by determining the imaging geometry of each of the two or more orientations of the angiographic imaging system from the projections of the plurality of non-invasive fiducial markers in the 2D angiographic images and the known 3D configuration of the plurality of non-invasive fiducial markers (operation 702). The method continues by identifying contours of a target vasculature in one or more of the plurality of 2D angiographic images (operation 703), back-projecting the contours of the target vasculature, through the imaging geometry of the two or more orientations, to a 3D object space (operation 704) and rendering a volume of the target vasculature in the 3D object space (operation 705). The method concludes by registering selected 2D angiographic images to a 3D scan volume (operation 706).

Figure 8:
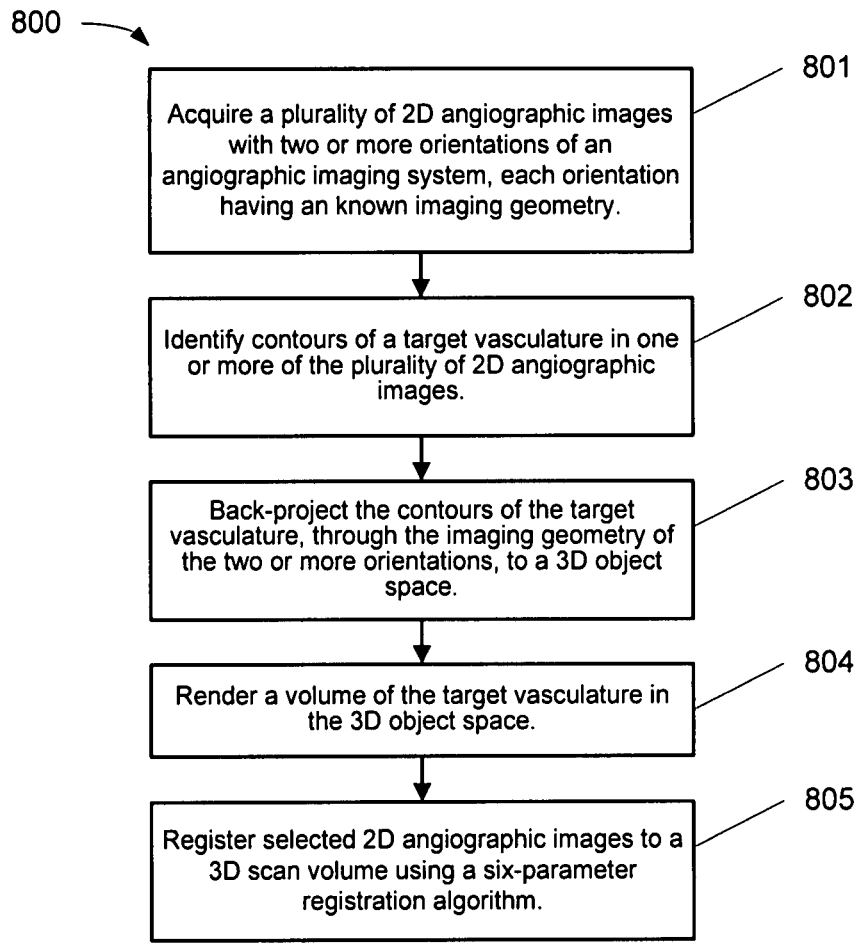
FIG. 8 is a flowchart illustrating a method in one embodiment.

FIG. 8 is a flowchart illustrating a method 800 in another embodiment of the present invention. Method 800 begins by acquiring a plurality of two-dimensional (2D) angiographic images, with two or more orientations of an angiographic imaging system, each orientation having a known imaging geometry (operation 801). The method continues by identifying contours of a target vasculature in one or more of the plurality of 2D angiographic images (operation 802), back-projecting the contours of the target vasculature, through the imaging geometry of the two or more orientations of the angiographic imaging system, to a 3D object space (operation 803) and rendering a volume of the target vasculature in the 3D object space (operation 804). The method concludes by registering selected 2D angiographic images to a 3D scan volume with a six-parameter registration algorithm (operation 805).

Figure 9:
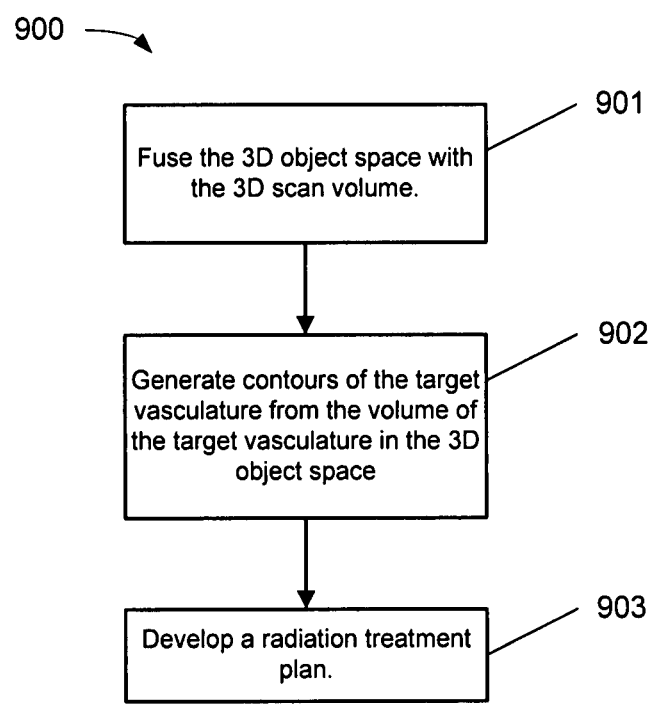
FIG. 9 is a flowchart illustrating a method in one embodiment.

FIG. 9 is a flowchart illustrating a method 900 further to method 700 and/or method 800 in one embodiment. Method 900 begins at operation 901, where the 3D object space of the angiographic imaging system is fused with the 3D scan volume. In operation 902, contours are generated in the 3D scan volume from the bounding volume of the target vasculature (nidus) in the 3D object space of the angiographic imaging system. In operation 903, the contours are used to develop the radiation treatment plan as described above.

In one embodiment, after the imaging geometry of the angiographic imaging system is determined, as described above, a reverse procedure may be used by a medical physicist that uses the 2D angiographic images as a quality assurance tool. The medical physicist may choose to identify contours of a target vasculature in the 3D scan volume. The contours of the target vasculature may then be projected through the imaging geometry of one or more orientations of the angiographic imaging system and displayed in the corresponding 2D angiographic image(s) to determine if the contours in the 3D scan volume conform with the target vasculature identified by contrast agent in the 2D angiographic images.

Figure 10:
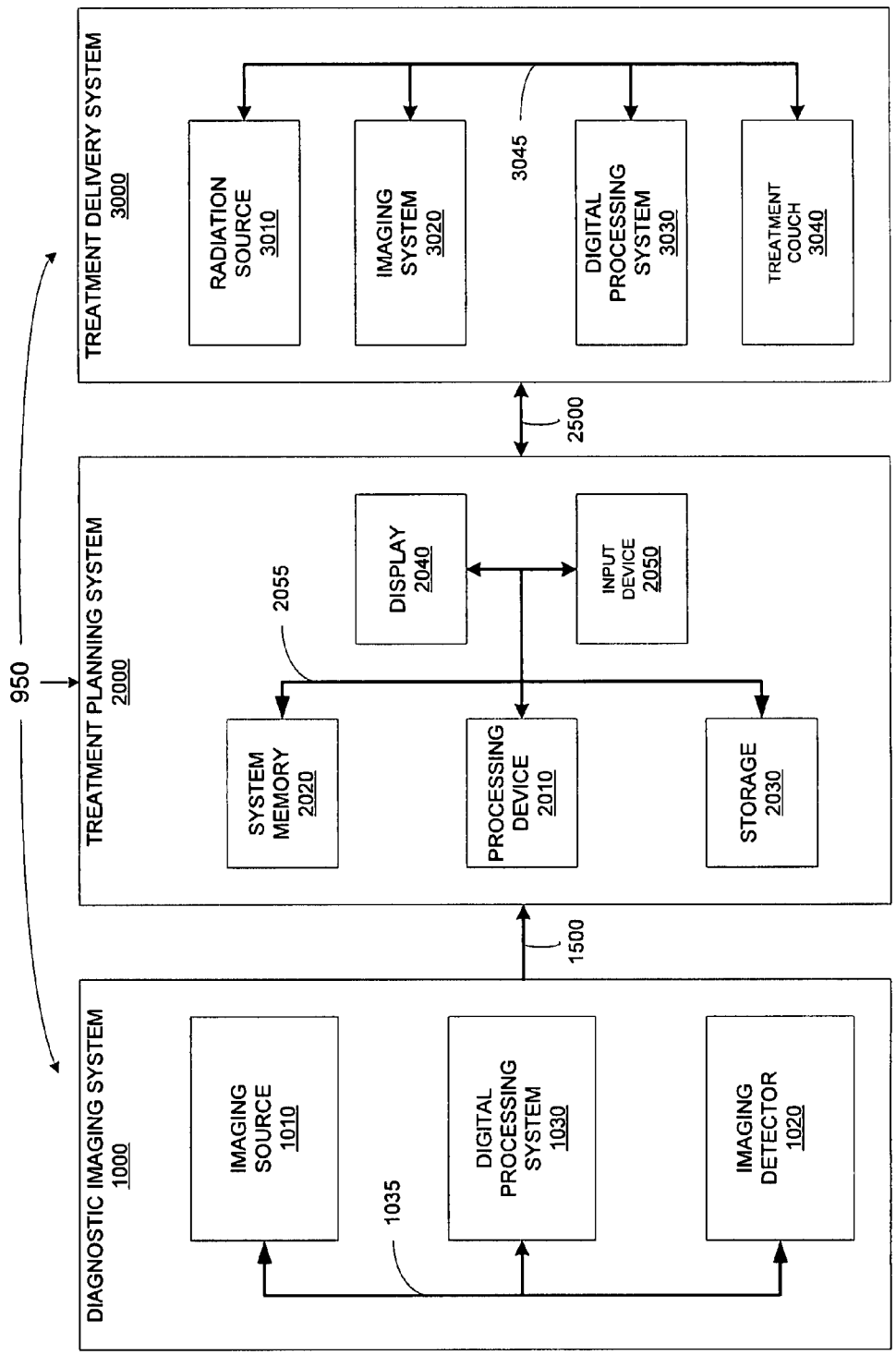
FIG. 10 is a bock diagram illustrating a system in which embodiment of the invention may be implemented.

FIG. 10 illustrates a system 950 in which embodiments of the present invention may be implemented. As described below and illustrated in FIG. 10, system 950 may include a diagnostic imaging system 1000, a treatment planning system 2000 and a treatment delivery system 3000.

Diagnostic imaging system 1000 may be any system capable of producing medical diagnostic images of a patient that may be used for subsequent medical diagnosis, treatment planning and/or treatment delivery. For example, diagnostic imaging system 1000 may be an angiographic imaging system (e.g., system 100), a computed tomography (CT) system, a magnetic resonance imaging (MRI) system, a positron emission tomography (PET) system, an ultrasound system or the like.

Diagnostic imaging system 1000 includes an imaging source 1010 to generate an imaging beam (e.g., x-rays) and an imaging detector 1020 to detect and receive the beam generated by imaging source 1010. In one embodiment, diagnostic imaging system 1000 may include two or more diagnostic X-ray sources and two or more corresponding imaging detectors. For example, two x-ray sources may be disposed around a patient to be imaged, fixed at an angular separation from each other (e.g., 90 degrees, 45 degrees, etc.) and aimed through the patient toward (an) imaging detector(s) which may be diametrically opposed to the x-ray sources. A single large imaging detector, or multiple imaging detectors, may also be used that would be illuminated by each x-ray imaging source. Alternatively, other numbers and configurations of imaging sources and imaging detectors may be used.

The imaging source 1010 and the imaging detector 1020 may be coupled to a digital processing system 1030 to control the imaging operation and process image data. Diagnostic imaging system 1000 includes a bus or other means 1035 for transferring data and commands among digital processing system 1030, imaging source 1010 and imaging detector 1020. Digital processing system 1030 may include one or more general-purpose processors (e.g., a microprocessor), special purpose processor such as a digital signal processor (DSP) or other type of device such as a controller or field programmable gate array (FPGA). Digital processing system 1030 may also include other components (not shown) such as memory, storage devices, network adapters and the like. Digital processing system 1030 may be configured to generate digital diagnostic images in a standard format, such as the DICOM (Digital Imaging and Communications in Medicine) format, for example. In other embodiments, digital processing system 1030 may generate other standard or non-standard digital image formats. Digital processing system 1030 may transmit diagnostic image files (e.g., the aforementioned DICOM formatted files) to treatment planning system 2000 over a data link 1500, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present invention to diagnose or treatment plan despite the existence of a physical separation between the system user and the patient.

Treatment planning system 2000 includes a processing device 2010 to receive and process image data, such as angiographic imaging data and 3D scan data as described above. Processing device 2010 may represent one or more general-purpose processors (e.g., a microprocessor), special purpose processor such as a digital signal processor (DSP) or other type of device such as a controller or field programmable gate array (FPGA). Processing device 2010 may be configured to execute instructions for performing treatment planning and/or image processing operations discussed herein, such as the spine segmentation tool described herein.

Treatment planning system 2000 may also include system memory 2020 that may include a random access memory (RAM), or other dynamic storage devices, coupled to processing device 2010 by bus 2055, for storing information and instructions to be executed by processing device 2010. System memory 2020 also may be used for storing temporary variables or other intermediate information during execution of instructions by processing device 2010. System memory 2020 may also include a read only memory (ROM) and/or other static storage device coupled to bus 2055 for storing static information and instructions for processing device 2010.

Treatment planning system 2000 may also include storage device 2030, representing one or more storage devices (e.g., a magnetic disk drive or optical disk drive) coupled to bus 2055 for storing information and instructions. Storage device 2030 may be used for storing instructions for performing the treatment planning steps discussed herein and/or for storing 3D imaging data and DRRs as discussed herein.

Processing device 2010 may also be coupled to a display device 2040, such as a cathode ray tube (CRT) or liquid crystal display (LCD), for displaying information (e.g., a 2D or 3D representation of the VOI) to the user. An input device 2050, such as a keyboard, may be coupled to processing device 2010 for communicating information and/or command selections to processing device 2010. One or more other user input devices (e.g., a mouse, a trackball or cursor direction keys) may also be used to communicate directional information, to select commands for processing device 2010 and to control cursor movements on display 2040.

It will be appreciated that treatment planning system 2000 represents only one example of a treatment planning system, which may have many different configurations and architectures, which may include more components or fewer components than treatment planning system 2000 and which may be employed with the present invention. For example, some systems often have multiple buses, such as a peripheral bus, a dedicated cache bus, etc. The treatment planning system 2000 may also include MIRIT (Medical Image Review and Import Tool) to support DICOM import (so images can be fused and targets delineated on different systems and then imported into the treatment planning system for planning and dose calculations), expanded image fusion capabilities that allow the user to treatment plan and view dose distributions on any one of various imaging modalities (e.g., MRI, CT, PET, etc.). Treatment planning systems are known in the art; accordingly, a more detailed discussion is not provided.

Treatment planning system 2000 may share its database (e.g., data stored in storage device 2030) with a treatment delivery system, such as treatment delivery system 3000, so that it may not be necessary to export from the treatment planning system prior to treatment delivery. Treatment planning system 2000 may be linked to treatment delivery system 3000 via a data link 2500, which may be a direct link, a LAN link or a WAN link as discussed above with respect to data link 1500. It should be noted that when data links 1500 and 2500 are implemented as LAN or WAN connections, any of diagnostic imaging system 1000, treatment planning system 2000 and/or treatment delivery system 3000 may be in decentralized locations such that the systems may be physically remote from each other. Alternatively, any of diagnostic imaging system 1000, treatment planning system 2000 and/or treatment delivery system 3000 may be integrated with each other in one or more systems.

Treatment delivery system 3000 includes a therapeutic and/or surgical radiation source 3010 to administer a prescribed radiation dose to a target volume in conformance with a treatment plan. Treatment delivery system 3000 may also include an imaging system 3020 to capture intra-treatment images of a patient volume (including the target volume) for registration or correlation with the diagnostic images described above in order to position the patient with respect to the radiation source. Imaging system 3020 may include any of the imaging systems described above. Treatment delivery system 3000 may also include a digital processing system 3030 to control radiation source 3010, imaging system 3020 and a patient support device such as a treatment couch 3040. Digital processing system 3030 may be configured to register 2D radiographic images from imaging system 3020, from two or more stereoscopic projections, with digitally reconstructed radiographs (e.g., DRRs from segmented 3D imaging data) generated by digital processing system 1030 in diagnostic imaging system 1000 and/or DRRs generated by processing device 2010 in treatment planning system 2000. Digital processing system 3030 may include one or more general-purpose processors (e.g., a microprocessor), special purpose processor such as a digital signal processor (DSP) or other type of device such as a controller or field programmable gate array (FPGA). Digital processing system 3030 may also include other components (not shown) such as memory, storage devices, network adapters and the like. Digital processing system 3030 may be coupled to radiation source 3010, imaging system 3020 and treatment couch 3040 by a bus 3045 or other type of control and communication interface.

Digital processing system 3030 may implement methods (e.g., such as method 1200 described above) to register images obtained from imaging system 3020 with pre-operative treatment planning images in order to align the patient on the treatment couch 3040 within the treatment delivery system 3000, and to precisely position the radiation source with respect to the target volume.

The treatment couch 3040 may be coupled to another robotic arm (not illustrated) having multiple (e.g., 5 or more) degrees of freedom. The couch arm may have five rotational degrees of freedom and one substantially vertical, linear degree of freedom. Alternatively, the couch arm may have six rotational degrees of freedom and one substantially vertical, linear degree of freedom or at least four rotational degrees of freedom. The couch arm may be vertically mounted to a column or wall, or horizontally mounted to pedestal, floor, or ceiling. Alternatively, the treatment couch 3040 may be a component of another mechanical mechanism, such as the Axum® treatment couch developed by Accuray Incorporated of Delaware, or be another type of conventional treatment table known to those of ordinary skill in the art.

Alternatively, treatment delivery system 3000 may be another type of treatment delivery system, for example, a gantry based (isocentric) intensity modulated radiotherapy (IMRT) system. In a gantry based system, a radiation source (e.g., a LINAC) is mounted on the gantry in such a way that it rotates in a plane corresponding to an axial slice of the patient. Radiation is then delivered from several positions on the circular plane of rotation. In IMRT, the shape of the radiation beam is defined by a multi-leaf collimator that allows portions of the beam to be blocked, so that the remaining beam incident on the patient has a pre-defined shape. The resulting system generates arbitrarily shaped radiation beams that intersect each other at the isocenter to deliver a dose distribution to the target region. In IMRT planning, the optimization algorithm selects subsets of the main beam and determines the amount of time that the patient should be exposed to each subset, so that the prescribed dose constraints are best met. In one particular embodiment, the gantry based system may have a gimbaled radiation source head assembly.

Embodiments of the present invention include various operations, which are described herein. These operations may be performed by hardware components, software, firmware or a combination thereof. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a machine-readable medium. These instructions may be used to program a general-purpose or special-purpose processor to perform the described operations. A machine-readable medium includes any mechanism for storing or transmitting information in a form (e.g., software, processing application) readable by a machine (e.g., a computer). The machine-readable medium may include, but is not limited to, magnetic storage medium (e.g., floppy diskette); optical storage medium (e.g., CD-ROM); magneto-optical storage medium; read-only memory (ROM); random-access memory (RAM); erasable programmable memory (e.g., EPROM and EEPROM); flash memory; electrical, optical, acoustical, or other form of propagated signal (e.g., carrier waves, infrared signals, digital signals, etc.); or another type of medium suitable for storing electronic instructions.

Additionally, some embodiments may be practiced in distributed computing environments where the machine-readable medium is stored on and/or executed by more than one computer system. In addition, the information transferred between computer systems may either be pulled or pushed across the communication medium connecting the computer systems such as in a remote diagnosis or monitoring system. In remote diagnosis or monitoring, a user may diagnose or monitor a patient despite the existence of a physical separation between the user and the patient. In addition, the treatment delivery system may be remote from the treatment planning system.

Although the operations of the method(s) herein are shown and described in a particular order, the order of the operations of each method may be altered so that certain operations may be performed in an inverse order or so that certain operation may be performed, at least in part, concurrently with other operations. In another embodiment, instructions or sub-operations of distinct operations may be in an intermittent and/or alternating manner. Additionally, some operations may be repeated within iteration of a particular method.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method, comprising:
acquiring a plurality of two-dimensional (2D) angiographic images with two or more orientations of an angiographic imaging system, each orientation having an unknown imaging geometry, wherein each of the plurality of 2D angiographic images includes a projection of a plurality of non-invasive fiducial markers having a known three-dimensional (3D) configuration;
registering, by a processing device, selected 2D angiographic images to a 3D scan volume produced by a 3D imaging system, wherein the imaging geometry of each orientation of the angiographic imaging system is unknown with respect to the 3D imaging system prior to acquiring the plurality of 2D angiographic images, wherein registering selected 2D angiographic images to the 3D scan volume comprises:
generating one or more sets of digitally reconstructed radiographs (DRRs) from the 3D scan volume using the imaging geometry of the two or more orientations of the angiographic imaging system;
comparing selected DRRs to the selected 2D angiographic images; and
finding a transformation between the 3D scan volume and the 3D object space that maximizes a similarity measure between the selected DRRs and the selected 2D angiographic images;
determining the imaging geometry of each of the two or more orientations of the angiographic imaging system from the projection of the plurality of non-invasive fiducial markers in each of the 2D angiographic images and the known 3D configuration of the plurality of non-invasive fiducial markers;
identifying contours of a target vasculature in one or more of the plurality of 2D angiographic images in each of the two or more orientations;
back-projecting the contours of the target vasculature, through the imaging geometry of the two or more orientations, to a 3D object space; and
rendering a volume of the target vasculature in the 3D object space.

2. The method of claim 1, wherein the plurality of non-invasive fiducial markers is arrayed on a non-invasive calibration device of known configuration, wherein the calibration device has a fixed location relative to a patient's head.

3. The method of claim 1, wherein the plurality of non-invasive fiducial markers is temporarily attached to a patient's head, the method further comprising determining the 3D configuration of the plurality of non-invasive fiducial markers by,
acquiring a calibrated 3D image of the patient, and
measuring the configuration of the plurality of non-invasive fiducial markers in the calibrated 3D image.

4. The method of claim 1, wherein the plurality of non-invasive fiducial markers comprise tracking objects temporarily attached to a patient's head, and wherein the configuration of the tracking objects is determined by a 3D tracking system.

5. The method of claim 1, wherein the target vasculature comprises a nidus of an arteriovenous malformation (AVM), wherein the plurality of 2D angiographic images comprises one or more time-series of angiographic images recording progress of a contrast agent from injection through infusion of the nidus, and wherein the selected 2D angiographic images include images without contrast agent and images with contrast agent.

6. The method of claim 5, wherein the selected 2D angiographic images comprise the images without contrast agent.

7. The method of claim 5, wherein the selected 2D angiographic images comprise the images with contrast agent.

8. The method of claim 1, wherein the similarity measure comprises an image intensity similarity measure, and wherein finding the transformation between the 3D scan volume and the 3D object space comprises applying a six-parameter registration algorithm to maximize the similarity measure.

9. The method of claim 1, further comprising:
fusing the 3D object space with the 3D scan volume using the transformation between the 3D scan volume and the 3D object space;
generating contours of the target vasculature from the volume of the target vasculature in the 3D object space; and
developing a radiation treatment plan.

10. A system, comprising:
a storage device; and a processing device operatively coupled with the storage device to:
  receive data comprising a plurality of two-dimensional (2D) angiographic images of an anatomical region in two or more different orientations of an angiographic imaging system, each orientation having an unknown imaging geometry, wherein each of the plurality of 2D angiographic images includes a projection of a plurality of non-invasive fiducial markers having a known three-dimensional (3D) configuration; and
  register data of selected 2D angiographic images with data comprising a calibrated 3D scan volume of the anatomical region produced by the 3D imaging system, wherein the imaging geometry of each orientation of the angiographic imaging system is unknown with respect to the 3D imaging system prior to the receive of data, wherein to register data of the selected 2D angiographic images to the 3D scan volume, the processing device is to:
  generate digitally reconstructed radiographs (DRRs) from the 3D scan volume using the imaging geometry of the two or more orientations of the angiographic imaging system;
  compare selected DRRs to the selected 2D angiographic images; and
  find a transformation between the 3D scan volume and the 3D object space that maximizes a similarity measure between the selected DRRs and the selected 2D angiographic images;
wherein the processing device is further to:
  determine the imaging geometry of each of the two or more orientations of the angiographic imaging system from the projection of the plurality of non-invasive fiducial markers in each of the 2D angiographic images and the known 3D configuration of the plurality of non-invasive fiducial markers;
  identify contours of a target vasculature in one or more of the plurality of 2D angiographic images in each of the two or more orientations;
  back-project the contours of the target vasculature, through the imaging geometry of the two or more orientations, to a 3D object space;
  render a volume of the target vasculature in the 3D object space;
  identify contours of a target vasculature in the 3D scan volume;
  project the contours of the target vasculature, through the imaging geometry of one or more orientations of the angiographic imaging system; and
  display the projections of the target vasculature in one or more 2D angiographic images.

11. The system of claim 10, wherein the target vasculature comprises a nidus of an arteriovenous malformation (AVM), wherein the plurality of 2D angiographic images comprises one or more time-series of angiographic images recording progress of a contrast agent from injection through infusion of the nidus, and wherein the selected 2D angiographic images include images without contrast agent and images with contrast agent.

12. The system of claim 11, wherein the selected 2D angiographic images comprise the images without contrast agent.

13. The system of claim 11, wherein the selected 2D angiographic images comprise the images with contrast agent.

14. The system of claim 10, wherein the similarity measure comprises an image intensity similarity measure, and wherein to find the transformation between the 3D scan volume and the 3D object space, the processing device is configured to apply a six-parameter registration algorithm to maximize the similarity measure.

15. The system of claim 10, wherein the processing device is further configured to:
  fuse the 3D object space with the 3D scan volume using the transformation between the 3D scan volume and the 3D object space; and
  generate contours of the target vasculature from the volume of the target vasculature in the 3D object space.

16. A non-transitory machine-readable medium including data that, when read by a processing device, cause the processing device to perform operations comprising:
  acquiring a plurality of two-dimensional (2D) angiographic images with two or more orientations of an angiographic imaging system, each orientation having an unknown imaging geometry, wherein each of the plurality of 2D angiographic images includes a projection of a plurality of non-invasive fiducial markers having a known three-dimensional (3D) configuration;
  registering selected 2D angiographic images to a 3D scan volume produced by a 3D imaging system, wherein the imaging geometry of each orientation of the angiographic imaging system is unknown with respect to the 3D imaging system prior to acquiring the plurality of 2D angiographic images, wherein registering selected 2D angiographic images to the 3D scan volume comprises:
    generating one or more sets of digitally reconstructed radiographs (DRRs) from the 3D scan volume using the imaging geometry of the two or more orientations of the angiographic imaging system;
    comparing selected DRRs to the selected 2D angiographic images; and
    finding a transformation between the 3D scan volume and the 3D object space that maximizes a similarity measure between the selected DRRs and the selected 2D angiographic images
  determining the imaging geometry of each of the two or more orientations of the angiographic imaging system from the projection of the plurality of non-invasive fiducial markers in each of the 2D angiographic images and the known 3D configuration of the plurality of non-invasive fiducial markers;
  identifying contours of a target vasculature in one or more of the plurality of 2D angiographic images in each of the two or more orientations;
  back-projecting the contours of the target vasculature, through the imaging geometry of the two or more orientations, to a 3D object space; and
  rendering a volume of the target vasculature in the 3D object space.

17. The non-transitory machine-readable medium of claim 16, wherein the plurality of non-invasive fiducial markers is arrayed on a non-invasive calibration device of known configuration, and wherein the calibration device has a fixed location relative to a patient's head.

18. The non-transitory machine-readable medium article of manufacture of claim 16, wherein the plurality of non-invasive fiducial markers is temporarily attached to a patient's head, wherein the machine-readable medium further includes data that cause the processing device to perform operations comprising:

determining the 3D configuration of the plurality of non-invasive fiducial markers by,
acquiring a calibrated 3D image of the patient, and
measuring the configuration of the plurality of non-invasive fiducial markers in the calibrated 3D image.

19. The non-transitory machine-readable medium of claim 16, wherein the plurality of non-invasive fiducial markers comprise tracking objects temporarily attached to a patient's head, and wherein the configuration of the tracking objects is determined by a 3D tracking system.

20. The non-transitory machine-readable medium of claim 16, wherein the target vasculature comprises a nidus of an arteriovenous malformation (AVM), wherein the plurality of 2D angiographic images comprises one or more time-series of angiographic images recording progress of a contrast agent from injection through infusion of the nidus, and wherein the selected 2D angiographic images include images without contrast agent and images with contrast agent.

21. The non-transitory machine-readable medium of claim 20, wherein the selected 2D angiographic images comprise the images without contrast agent.

22. The non-transitory machine-readable medium of claim 20, wherein the selected 2D angiographic images comprise the images with contrast agent.

23. The non-transitory machine-readable medium of claim 16, wherein the similarity measure comprises an image intensity similarity measure, and wherein finding the transformation between the 3D scan volume and the 3D object space comprises applying a six-parameter registration algorithm to maximize the similarity measure.

24. The non-transitory machine-readable medium of claim 16, wherein the machine-readable medium further includes data that cause the processing device to perform operations comprising:
fusing the 3D object space with the 3D scan volume using the transformation between the 3D scan volume and the 3D object space;
generating contours of the target vasculature from the volume of the target vasculature in the 3D object space; and
developing a radiation treatment plan.

* * * * *